US011389302B2

(12) United States Patent
Lauf et al.

(10) Patent No.: US 11,389,302 B2
(45) Date of Patent: Jul. 19, 2022

(54) SPINAL FACET JOINT AND LAMINOPLASTY IMPLANT

(71) Applicant: Life Spine, Inc., Huntley, IL (US)

(72) Inventors: Garrett D. Lauf, Hampshire, IL (US); Matthew S. Coyne, Algonquin, IL (US); Forrest Samuel, Carlsbad, CA (US)

(73) Assignee: Life Spine, Inc., Huntley, IL (US)

( * ) Notice: Subject to any disclaimer, the term of this patent is extended or adjusted under 35 U.S.C. 154(b) by 251 days.

(21) Appl. No.: 16/746,807

(22) Filed: Jan. 18, 2020

(65) Prior Publication Data
US 2020/0179129 A1 Jun. 11, 2020

Related U.S. Application Data

(60) Provisional application No. 62/945,069, filed on Dec. 6, 2019, provisional application No. 62/776,181, filed on Dec. 6, 2018.

(51) Int. Cl.
*A61F 2/44* (2006.01)
*A61B 17/70* (2006.01)
*A61F 2/30* (2006.01)

(52) U.S. Cl.
CPC ........ *A61F 2/4405* (2013.01); *A61B 17/7071* (2013.01); *A61F 2002/3093* (2013.01); *A61F 2002/30153* (2013.01); *A61F 2002/30985* (2013.01)

(58) Field of Classification Search
CPC ............ A61B 17/7071; A61B 17/7062; A61B 17/7064; A61F 2/4405
See application file for complete search history.

(56) References Cited

U.S. PATENT DOCUMENTS

| 2005/0261688 A1* | 11/2005 | Grady, Jr. | .......... A61B 17/8014 |
| | | | 606/286 |
| 2006/0247650 A1 | 11/2006 | Yerby et al. | |
| 2009/0270929 A1* | 10/2009 | Suddaby | ............ A61B 17/1655 |
| | | | 606/324 |
| 2009/0326589 A1 | 12/2009 | Lemoine et al. | |
| 2013/0060283 A1* | 3/2013 | Suh | ..................... A61B 17/7071 |
| | | | 606/246 |
| 2015/0342648 A1* | 12/2015 | McCormack | ...... A61B 17/7002 |
| | | | 606/247 |
| 2020/0375633 A1* | 12/2020 | McCormack | ...... A61B 17/7064 |

FOREIGN PATENT DOCUMENTS

WO 2014078798 A1 5/2014

* cited by examiner

*Primary Examiner* — Julianna N Harvey
(74) *Attorney, Agent, or Firm* — Foley & Lardner LLP

(57) ABSTRACT

A spine implant for use in spinal facet joint fixation or to connect distracted portions of a vertebral lamina in a laminoplasty through use or non-use of a spacer. One or two bone screw plates are angularly adjustable relative to a base plate for attachment by bone screws to vertebral bone. One form of the spine implant has a base plate, a first plate pivotally connected to the base plate for angular adjustment relative to the base plate and configured to hold one or two bone screws for attaching the first plate to first vertebral bone, and a second plate configured to hold two bone screws for attaching the second plate to second vertebral bone. The second plate may be pivotally connected to the body for angular adjustment of the second plate relative to the base plate or fixed to the base plate at a predetermined angle.

5 Claims, 16 Drawing Sheets

SPINAL FACET JOINT AND LAMINOPLASTY IMPLANT

CROSS-REFERENCE TO RELATED APPLICATIONS

This U.S. non-provisional patent application claims the benefit of and/or priority under 35 U.S.C. § 119(e) to U.S. provisional patent application Ser. No. 62/945,069 filed Dec. 6, 2019 titled "Spinal Facet Joint and Laminoplasty Implant," the entire contents of which is specifically incorporated herein by reference.

FIELD OF THE INVENTION

The present invention relates to orthopedic implants for the spine and, more particularly, to orthopedic implants for spinal facet joint fixation and laminoplasty.

BACKGROUND OF THE INVENTION

Vertebrae of the spine are linked to one another through an intervertebral disc, a left facet joint, and a right facet joint. This joint combination controls movement of the vertebrae relative to one another. The left facet joint has a pair of articulating surfaces located on the left side of the vertebrae, while the right facet joint has a second pair of articulating surfaces located on the right side of the vertebrae. Each pair of articulating surfaces includes a superior articular surface and an inferior articular surface. Together, the superior and inferior articular surfaces of adjacent vertebra form the facet joint. Being synovial joints, each facet joint is surrounded by a capsule of connective tissue and produces a fluid to lubricate the joint. The joint surfaces are coated with cartilage allowing the joints to articulate relative to one another.

Facet joints of the spine are in almost constant motion. Because of this, spinal facet joints in many people simply wear out. When facet joints become worn or torn, the cartilage may become thin or disappear. This can cause a reaction of the bone of the joint underneath—producing, e.g., overgrowth of bone spurs, an enlargement of the joints, and causing back pain. In other instances, the facet joint undergoes degradation and/or deterioration due to disease, injury, use, or other cause. All of the above and other conditions are commonly referred to as "spinal facet joint disease," "spinal facet joint syndrome," "spinal facet joint condition" or other names, and are hereinafter collectively, "spinal facet joint disorders" or simply "facet joint disorders." Spinal facet joint disorders are thus some of the most common of all recurring neck and back problems, with some of them causing serious physical symptoms such as severe pain, reduced immobility, and even disability.

One form of treatment for spinal facet disorders is surgery. A commonly used surgical method involves immobilizing (fixing) the spinal facet joint. In these procedures an implant is installed on or relative to the spinal facet joint. Allograft or other appropriate material for promoting bone fusion may or may not be introduced into or carried by the implant. Typically, a configured body is delivered to the facet joint with a separate plate that is fastened to the configured body and to one or more of the affected adjacent vertebrae at or in the facet joint.

Another problem of the spine is spinal stenosis. Spinal stenosis is a condition where there is narrowing of the spinal canal (and often the neural foramen), which causes compression of the spinal cord and/or nerve roots. This narrowing is caused by numerous factors including bone spurs, degeneration of the intervertebral disks and facet joints, and thickening of the ligaments. Spinal stenosis can produce pain and/or numbness in the arms, clumsiness of the hands, and gait disturbances. The spine may also undergo other compression problems. If left untreated, such problems can lead to a loss in mobility and/or permanent physical damage.

One manner of treating spinal stenosis and other spinal compression conditions, especially, but not necessarily, the cervical spine, is a laminoplasty. In a laminoplasty, the spinal canal is expanded by repositioning the lamina rather than removing it completely, as in a laminectomy. Decompression is provided while maintaining the stabilizing effects of the posterior portion of the vertebra through retention of a portion of the posterior portion of the vertebra. The advantage of a laminoplasty is that it increases the size of the spinal canal but leaves a posterior portion that helps keep the spine stable.

In a laminoplasty, one side of a lamina is cut through while the other side of the lamina is grooved to create a "hinged" or "swinging" flap or door of bone. The lamina bone flap is then opened (thereby enlarging the spinal canal) to relieve pressure on the spinal cord. An implant is placed between the free side of the lamina and the cut vertebra portion. The implant is then attached to the body, the lamina bone flap, and the cut vertebra in order to fix the position of the lamina bone flap and the enlarged spinal canal.

The above laminoplasty approach, however, has various drawbacks. For instance, the pre-defined geometry of laminoplasty bodies can create the need for in-situ contouring. Additionally, pre-bent laminoplasty plates and/or other laminoplasty components having pre-defined configurations can add numerous iterations to the installation procedure. As is well known, the longer and more complicated the procedure, the greater the likelihood for problems.

There thus exists a need for a more versatile spinal facet joint and laminoplasty implant.

SUMMARY OF THE INVENTION

A spine implant is usable for spinal facet joint fixation or for connecting a distracted lamina in a laminoplasty. The spinal implant has a base plate, base, first plate, or body (collectively, base plate) that accepts a block or spacer for use as the spinal facet joint fixator or without the block/spacer for the laminoplasty distracted lamina connector. A first bone screw plate is pivotally connected to one end of the base plate and retains one or more bone screws for attachment to first vertebral bone. A second bone screw plate is either pivotally connected to another end of the base plate or is fixed in angular orientation relative to the base plate and has two or more bores that each retain bone screws for attachment to second vertebral bone.

The base plate has either one swivel, hinge, pivot, or pivot structure, or two swivels, hinges, pivots, or pivot structures that pivotally connect the first bone screw plate and the second bone screw plate to the base plate depending on its form. The pivot structures can be dowels press fit and welded into the base plate of the plate assembly (implant) and slip fit into the screw ends, allowing the bone screw plates to pivot about the dowel hinge. Other structures are contemplated and may be used.

In the case of a single pivoting bone screw plate, the bone screw plate or side opposite of the pivoting bone screw plate can be made in a variety of angles relative to the base plate. The base plate has a thru hole which allows a connector, fastener, attachment component, or the like (e.g. a lag screw) to pass through the base plate for connection to the wedge.

The bone screw holes of the bone screw plates have female threading that interfaces with male threading on the underside of the head of the bone screw. The bone screws are retained by the bone screw plates and placed into vertebral bone such as the lateral mass or spinous process of the spine.

The spacer, block or wedge component of the present spine implant has teeth, serrations or the like on opposite faces that interface with vertebral bone to help prevent motion. There is a female machine thread that accepts the male thread of the lag screw. There is a cutout on the sides of the spacer to aid in installation of the spacer, and a thru hole on the faces of the spacer that allows bone to grow through the spacer.

The lag screw has machine threads at its tip that connect to the spacer and a face that interferes with the base plate. The lag screw has a male drive feature that allows the screw to be driven into the spacer and a female thread that connects to a driver to ensure that it does not fall off of the driver.

The bone screws have a thread on the end to interface with the bone, and a male threading on the underside of the head to interface with the female threading the bone screw plates. There is a male drive feature (e.g. a configured boss) that allows the bone screw to be driven (installed) into vertebral bone, and female threading within the drive feature that connects to the driver to ensure the bone screw does not fall off of the driver.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features, characteristics, structures, elements and/or the like of the present invention will be more fully understood from the following detailed description taken in conjunction with the accompanying drawings, wherein.

DETAILED DESCRIPTION OF THE INVENTION

The present invention with various forms will now be described to provide an overall understanding of the principles of the structure, function, manufacture, and use of the devices and methods disclosed herein. Those skilled in the art will understand that the devices and methods specifically described herein and illustrated in the accompanying drawings are non-limiting forms and that the scope of the present invention is defined solely by the claims. The features illustrated and/or described in connection with a form may be combined with the features of other forms. Such modifications and variations are intended to be included within the scope of the present invention, but not limiting thereof.

Components of the various forms of the present spine implant can be adapted in various manners (e.g., selection of material, dimensions, surface features, etc.) so as to provide a spine implant capable of adapting to various facet joint configurations and laminoplasty cuts/lamina shapes. Additionally, various components of the spine implant can include a fusion-promoting bioactive material, allograft, or the like capable of actively promoting bone growth. The various components of the present spine/spinal implant are made from the biocompatible material. Various manufacturing processes may be used include 3-D printing.

FIGS. 1-26 show a dual pivot form of a spine or spinal implant (spine implant), generally designated 10, and its components, configured for spinal facet joint fixation. As described below with reference to FIG. 31, a dual pivot form of a spine or spinal implant (spine implant), generally designated 10a, is configured for a laminoplasty. As described below with reference to FIGS. 27-28, a single pivot form of a spine or spinal implant (spine implant), generally designated 120, is configured for spinal facet joint fixation. All of the spine implants 10, 10a, 120 are fashioned in accordance with the principles of the present invention. Other configurations are contemplated.

Figure 1:
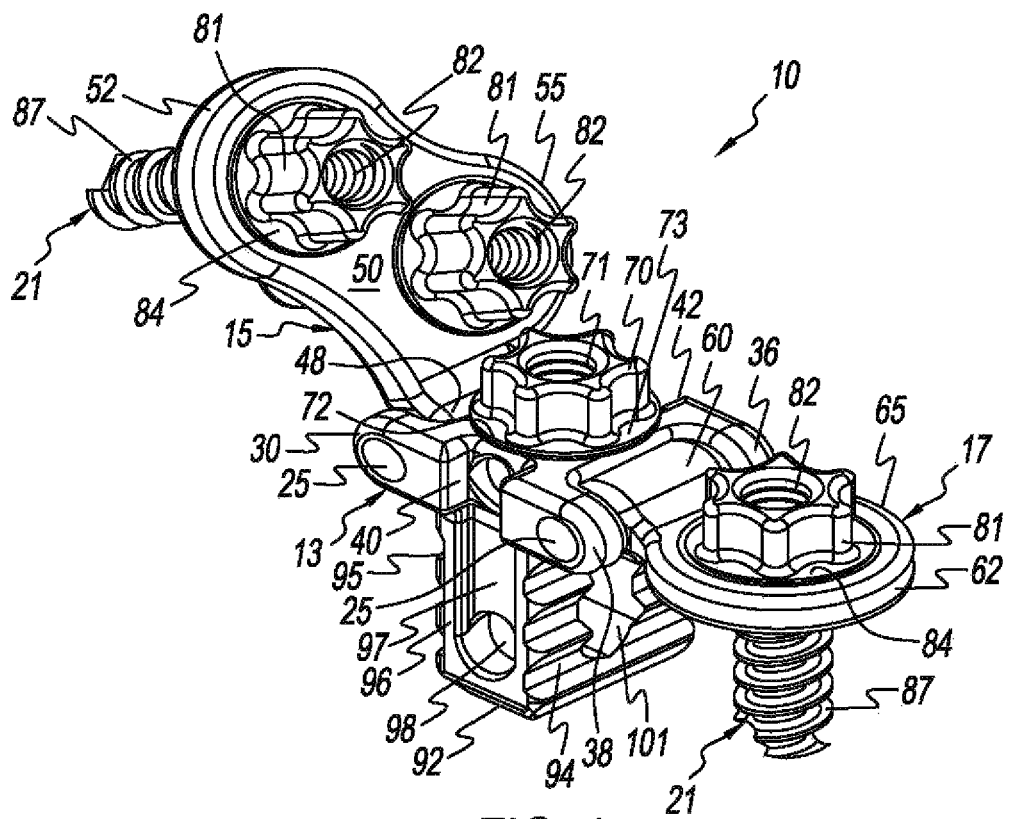
FIG. 1 is a view of a dual pivot form of the present spine implant.
Figure 2:
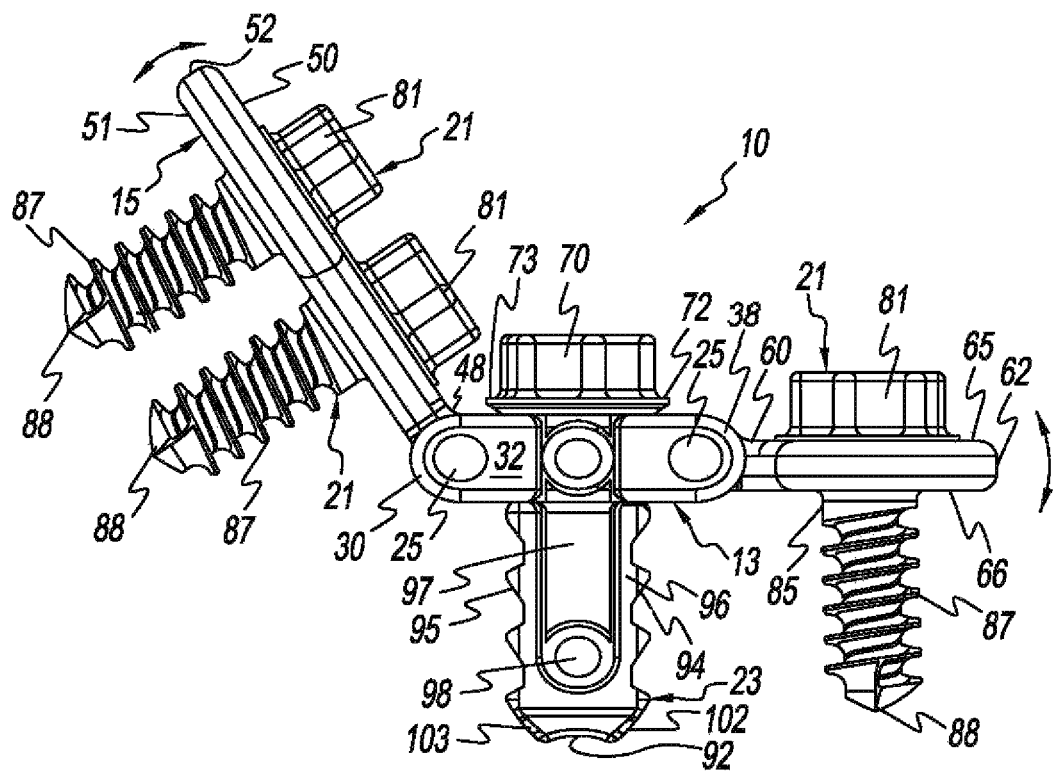
FIG. 2 is a side view of the dual pivot spine implant of FIG. 1.
Figure 3:
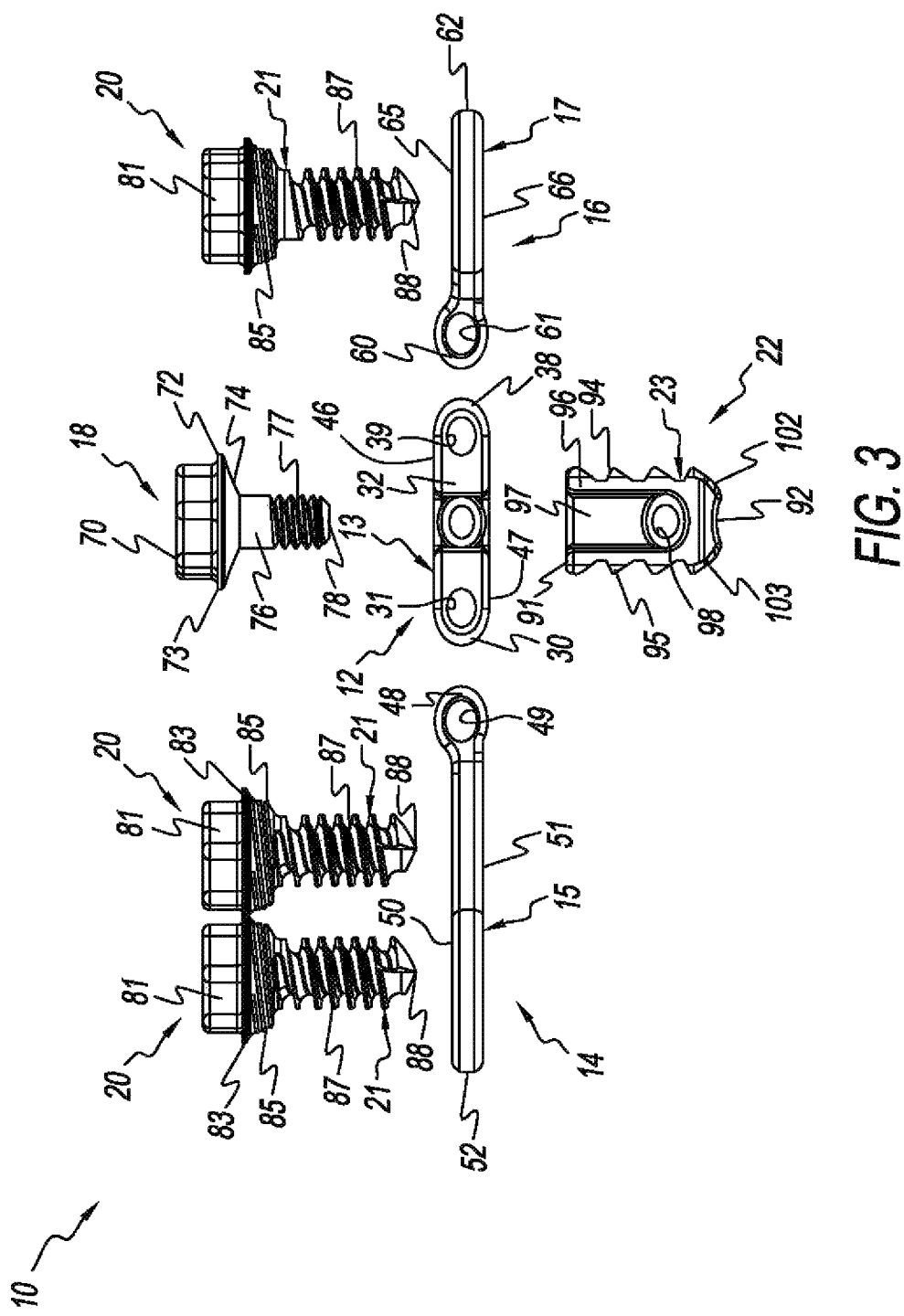
FIG. 3 is an exploded side view of the dual pivot spine implant of FIG. 1.
Figure 4:
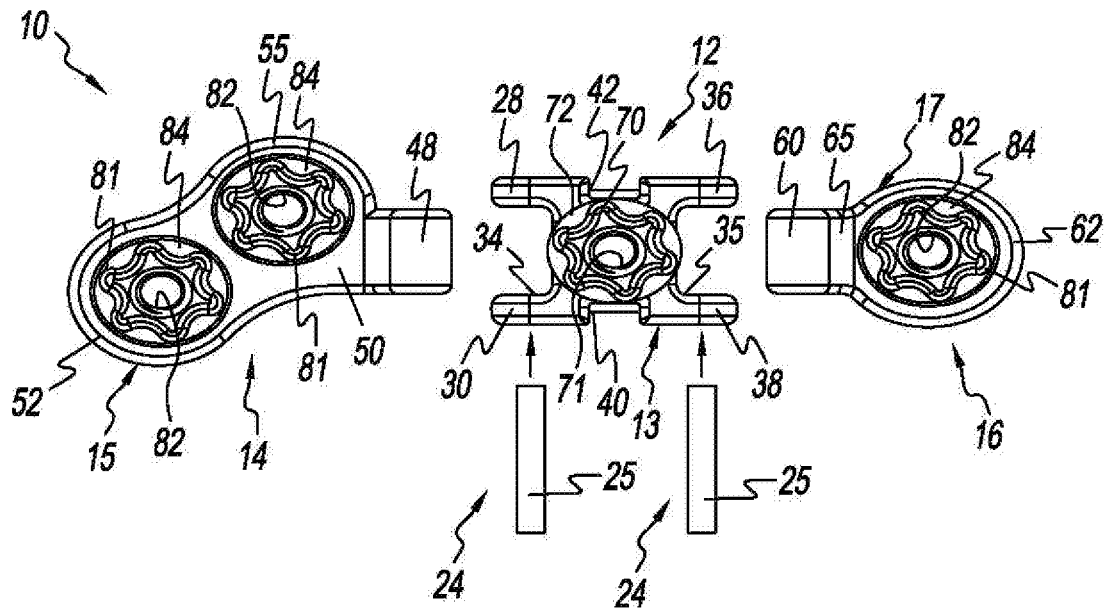
FIG. 4 is an exploded top view of the dual pivot spine implant of FIG. 1.
Figure 5:
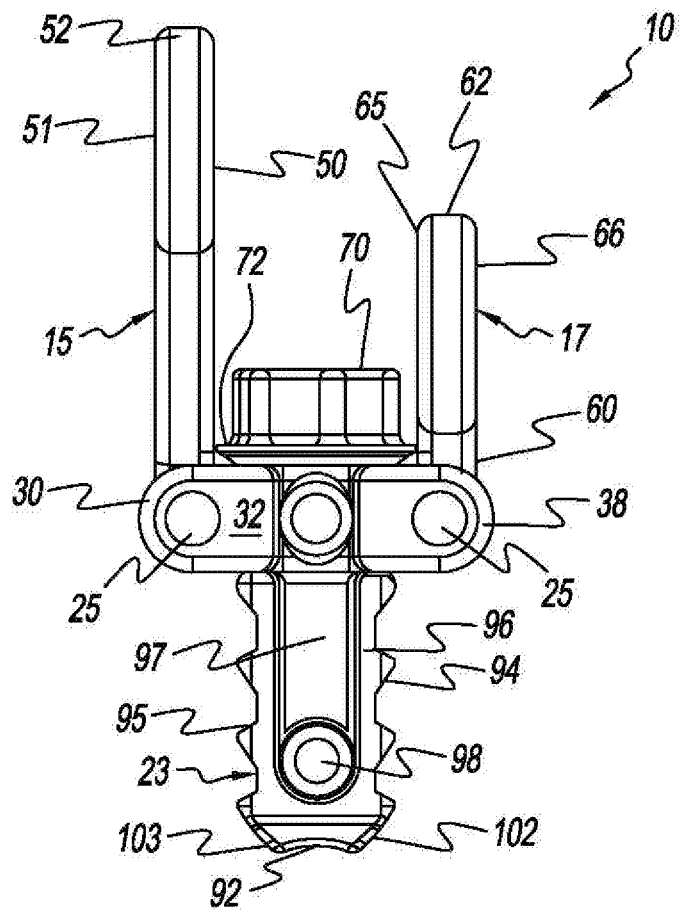
FIG. 5 is side view of the dual pivot spine implant of FIG. 1 with the two pivoting bone screw plates thereof in a fully upward position.
Figure 6:
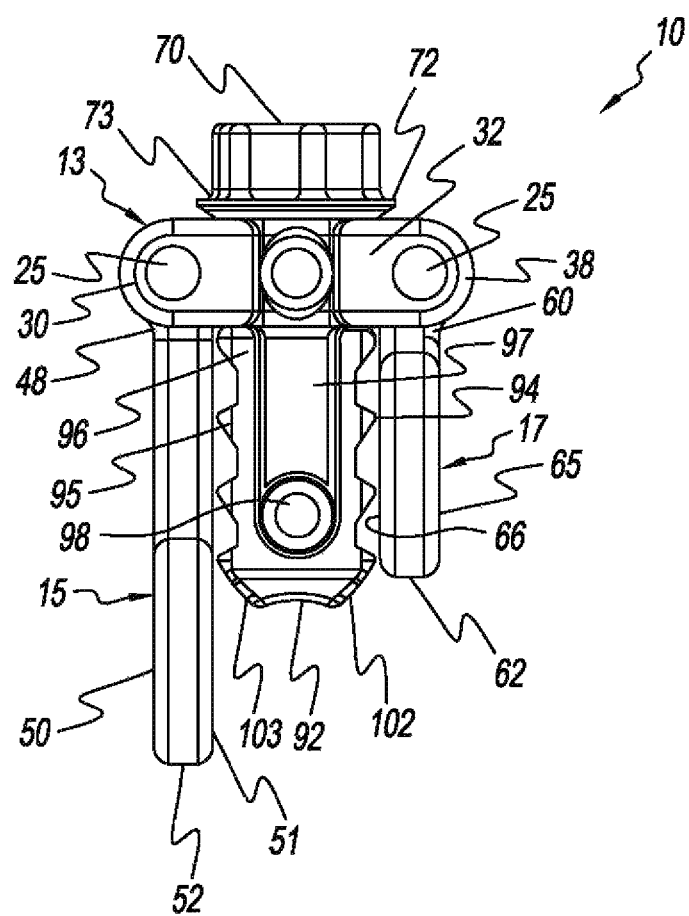
FIG. 6 is a side view of the dual pivot spine implant of FIG. 1 with the two pivoting bone screw plates thereof in a fully downward position.
Figure 29:
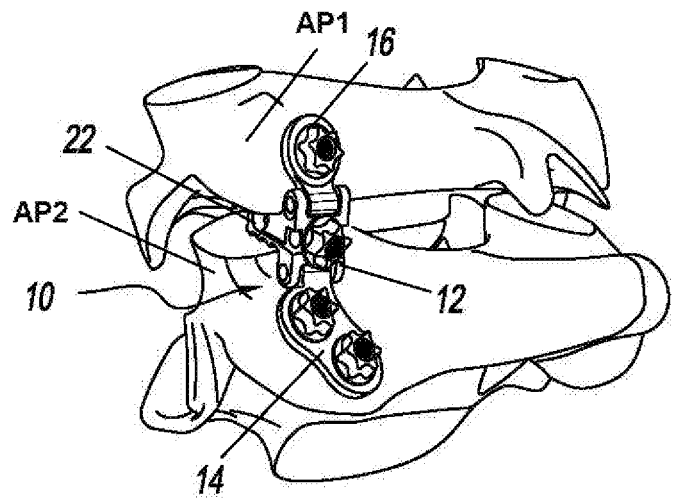
FIG. 29 is a rendering of a spinal facet joint with the dual pivot spine implant of FIG. 1 installed therein.
Figure 30:
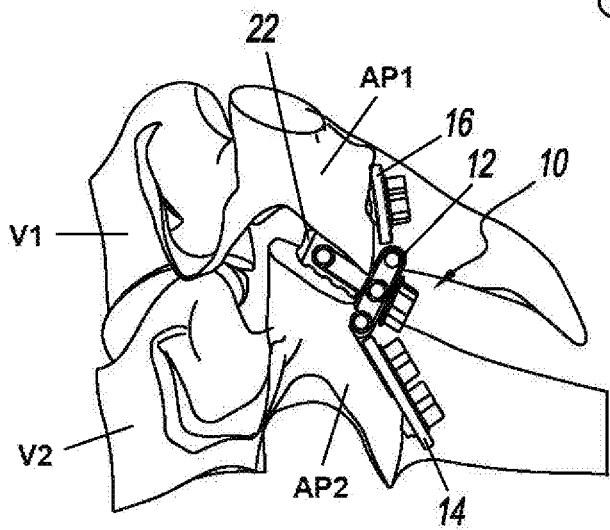
FIG. 30 is a rendering of another view of a spinal facet joint with the dual pivot spine implant of FIG. 1 installed therein.
Figure 31:
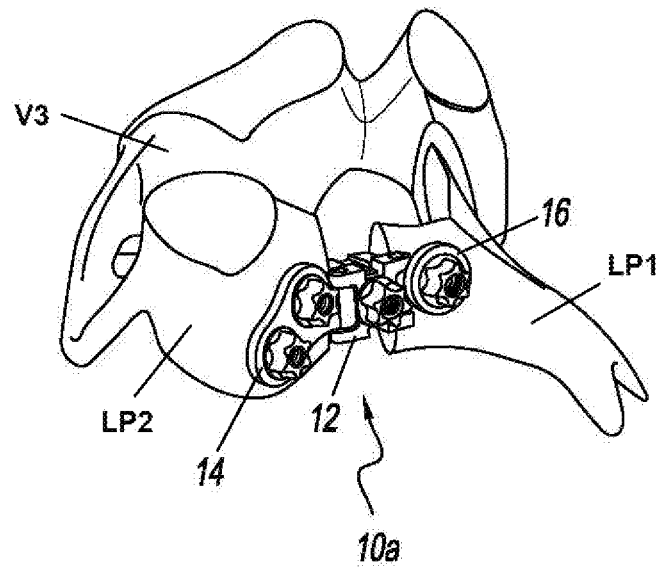
FIG. 31 is a rendering of a distracted spinal lamina as a result of a laminoplasty with a form of the dual pivot spine implant of FIG. 1 without the spacer installed between the distracted spinal lamina.

As shown in FIGS. 1-6, the spine implant 10 has a base plate, base, body or the like 12 (collectively, base plate 12), a dual bone screw plate 14 that is pivotally connected to the base plate 12 such that the dual bone screw plate 14 swivels so the angular orientation of the dual bone screw plate 14 may be varied as necessary, a single bone screw plate 16 that is pivotally connected to the base plate 12 such that the single bone screw plate 16 swivels so the angular orientation of the single bone screw plate 16 may be varied as necessary, a spacer, block, wedge or the like 22 (collectively spacer 22), and a fastener, coupling, attachment component or the like 18 (collectively, fastener 18) shown as a lag screw, understanding that different types of fasteners may be used, to connect the spacer 22 to the base plate 12. Bone screws 20 are used to attach the bone screw plates 14 and 16 to vertebral bone for spinal facet joint fixation such as seen in FIGS. 29-30 and for connection to distracted lamina portions as seen in FIG. 31. Being pivotally connected together, the single bone screw plate 16 may be oriented in various angles relative to the base plate 12. In the facet joint fixation implant form 10, the dual bone screw plate 16, being pivotally connected to the base plate 12, may be oriented in various angles relative to the base plate 12. FIGS. 5 and 6 illustrate the range of angular movement of the single bone screw plate 16 relative to the base plate 12 and of the dual bone screw plate 14 relative to the base plate 12.

Figure 7:
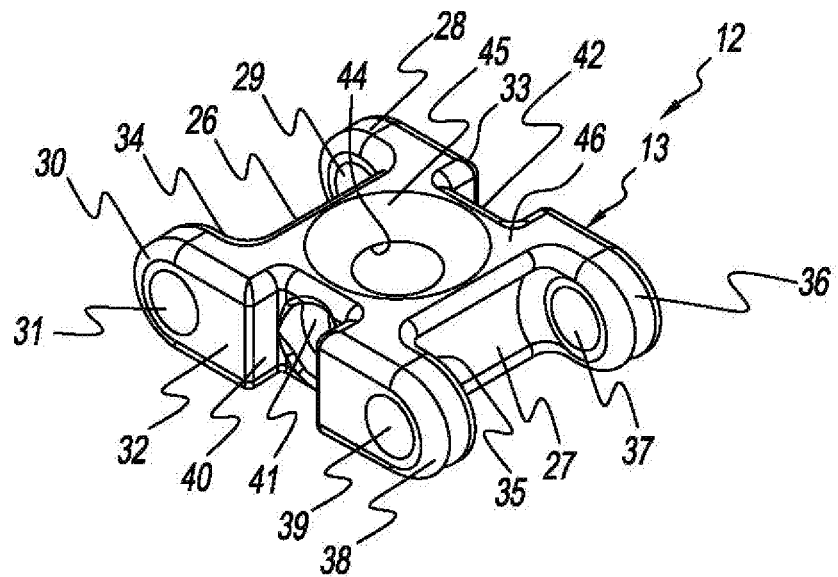
FIG. 7 is a view of the base plate or body of the dual pivot spine implant of FIG. 1.
Figure 8:
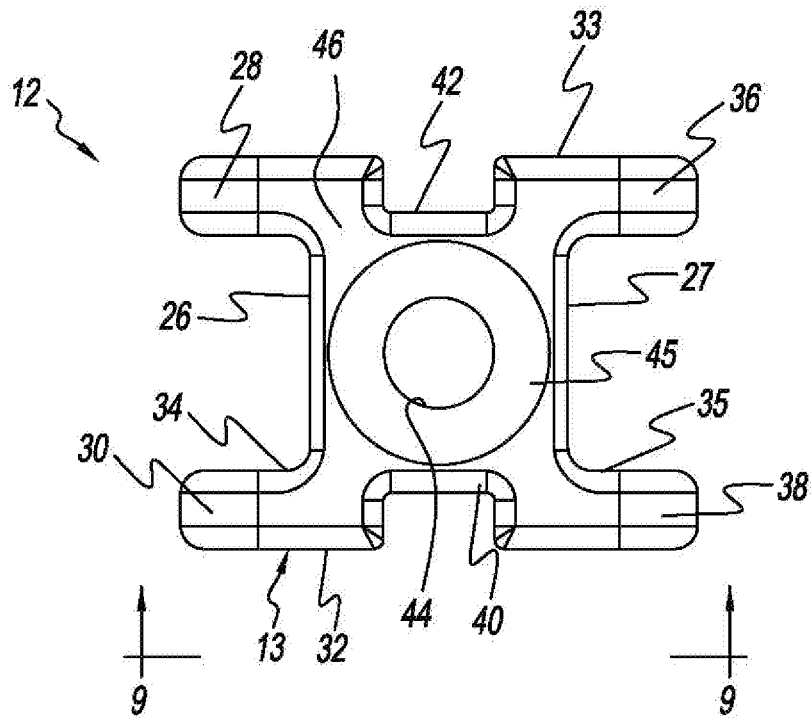
FIG. 8 is a top view of the base plate of the dual pivot spine implant of FIG. 7.
Figure 9:
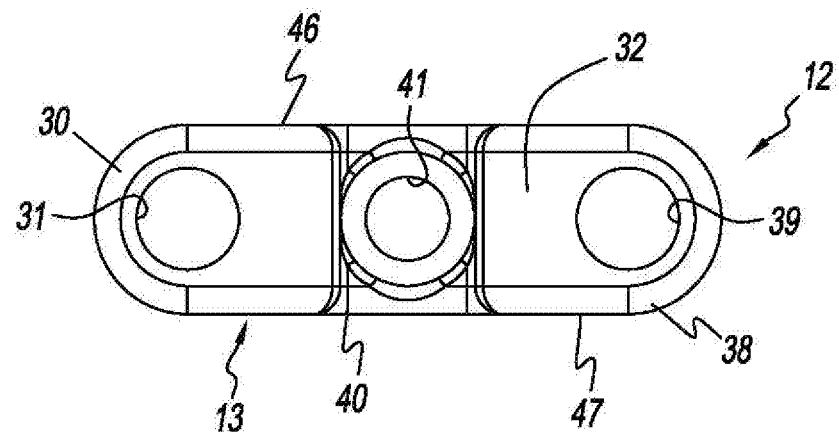
FIG. 9 is a side view of the base plate of the dual pivot spine implant of FIG. 7 taken along line 9-9 of FIG. 8.

FIGS. 7-9 specifically show the base plate 12. The base plate 12 is one component of the spine implant 10. The base plate 12 has a body 13 in the general shape of an "H", with a substantially planar or flat upper surface or top 46 and a substantially planar or flat lower surface or bottom 47. A bore 44 extends through the body 13 from the upper surface 46 to the lower surface 47. A countersink 45 surrounds the bore 44 on the upper surface of the base 12. The bore 44 is sized to receive the lag screw 18. The base plate 12 defines a first end 26 having a first flange or projection 30 extending from a first lateral side 32, and a second flange or projection 28 extending from a second lateral side 33, the nomenclature first and second, being arbitrary here and throughout unless indicated otherwise. The first flange 30 has a first bore 31 therein. The second flange 28 has a second bore 29 therein. The first and second flanges 30, 28 form a first notch 34 at the first end 26, the first notch 34 configured to receive a boss 48 of the dual bone screw plate 14. The first and second bores 31, 29 are configured to receive a pivot pin 24 (see, e.g., FIG. 4).

The base plate 12 further defines a second end 27 having a third flange or projection 38 extending from the first lateral side 32, and a fourth flange or projection 36 extending from the second lateral side 33, the nomenclature third and fourth, being arbitrary here and throughout unless indicated otherwise. The third flange 38 has a third bore 39 therein. The fourth flange 36 has a fourth bore 37 therein. The third and fourth flanges 38, 36 form a second notch 35 at the second end 27, the second notch 35 configured to receive a boss 60 of the single bone screw plate 16. The third and fourth bores 39, 37 are configured to receive a pivot pin 24 (see, e.g., FIG. 4).

A first hinge, pivot, hinge, pivot structure or the like, is created by the first notch 34 of the base plate 12, the first flange 30 and associated hole 31, the second flange 28 and associated hole 29, pivot pin 24, and the boss 48 and associated bore 49 of the dual bone plate 14. The boss 48 of the dual bone plate 14, and thus the dual bone plate 14, swivels relative to the base plate 12. A second hinge, pivot, hinge, pivot structure or the like, is created by the second notch 35 of the base plate 12, the third flange 38 and associated hole 39, the fourth flange 36 and associated hole 37, pivot pin 24, and the boss 60 and associated bore 61 of the single bone plate 16. The boss 60 of the single bone plate 16, and thus the single bone plate 16, swivels relative to the base plate 12.

The first lateral side 32 includes a first cutout 40 with a first cutout hole 41. The second lateral side 33 includes a second cutout 42 with a second cutout hole 43. The first and second cutouts 40, 42 along with the first and second holes 41, 43, provide a manner of aiding in installation of the base plate 12. An installation instrument (not shown) may be received by the cutouts and holes. Additionally, the holes may allow bone ingrowth. The cutout 40 aligns with the channel 97 of the spacer 22, while the cutout 42 aligns with the channel 100 of the spacer 22.

Figure 10:
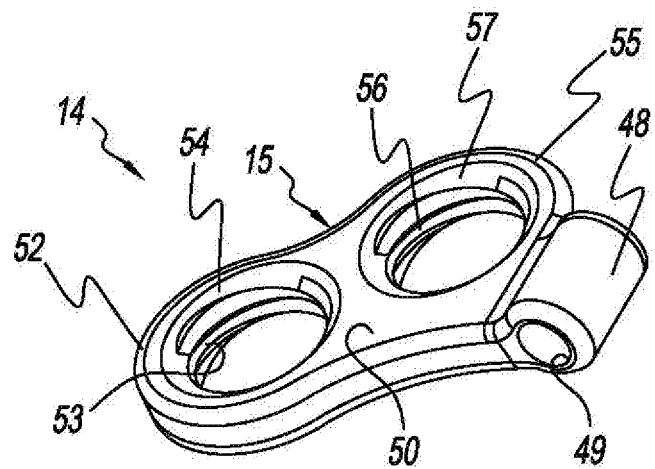
FIG. 10 is a view of the double bone screw plate or end of the dual pivot spine implant of FIG. 1.
Figure 11:
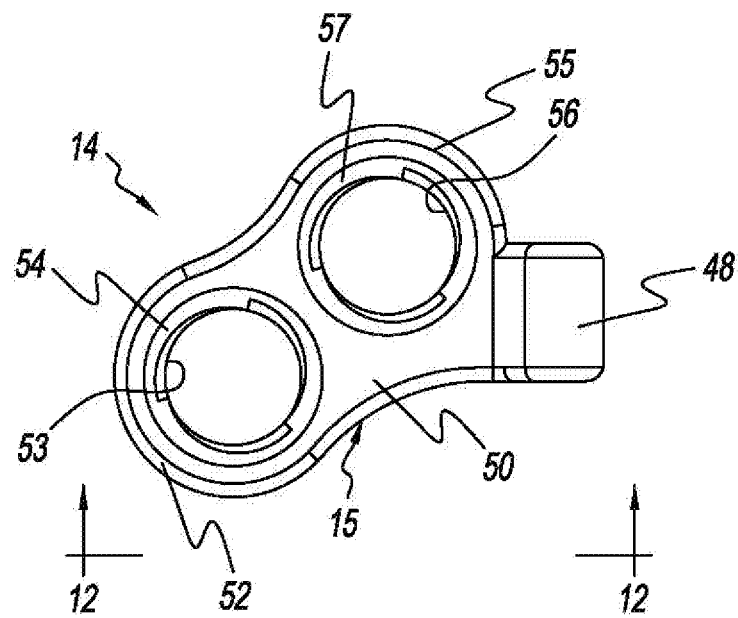
FIG. 11 is a top view of the double bone screw plate of FIG. 10.
Figure 12:
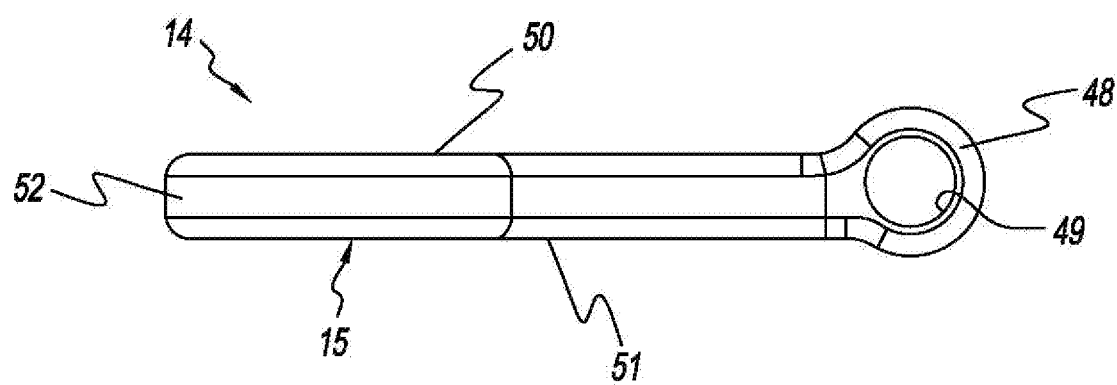
FIG. 12 is a side view of the double bone screw plate of FIG. 10 taken long line 12-12 of FIG. 11.

FIGS. 10-12 show the dual bone screw plate 14. The dual bone screw plate 14 has a body 15 with an upper side 50 and a lower side 51. The lower side 51 is substantially planar and is configured for placement against vertebral bone. The upper side 50 is also substantially planar. The body 15 has a boss, extension, projection or the like 48 having a bore 49 extending through the boss 48. The bore 49 is configured to receive the pivot pin 24. The boss 48 is sized for reception in the first notch 34 of the base plate 12. The boss 48 connects to the base plate 12 via a pivot pin 24.

A first, internally threaded bone screw bore 54 is provided at an end 52 of the body 15. The first, internally threaded bone screw bore 54 extends from the upper side 50 to the lower side 51. A countersink 54 is provided about the first, internally threaded bone screw bore 54 on the upper side 50 of the body 15. The first, internally threaded bone screw bore 54 is configured to receive and hold a bone screw 20. Particularly, the shaft 75 of the bone screw 20 is able to extend through the first, internally threaded bone screw bore 54 while the externally threaded underside 85 of the head 81 of the bone screw 20 threadedly mates with the first, internally threaded bone screw bore 54. A second, internally threaded bone screw bore 56 is provided at a middle 55 of the body 15. The second, internally threaded bone screw bore 56 extends from the upper side 50 to the lower side 51. A countersink 57 is provided about the second, internally threaded bone screw bore 56 on the upper side 50 of the body 15. The second, internally threaded bone screw bore 56 is configured to receive and hold a bone screw 20. Particularly, the shaft 75 of the bone screw 20 is able to extend through the second, internally threaded bone screw bore 56 while the externally threaded underside 85 of the head 81 of the bone screw 20 threadedly mates with the second, internally threaded bone screw bore 54.

Figure 13:
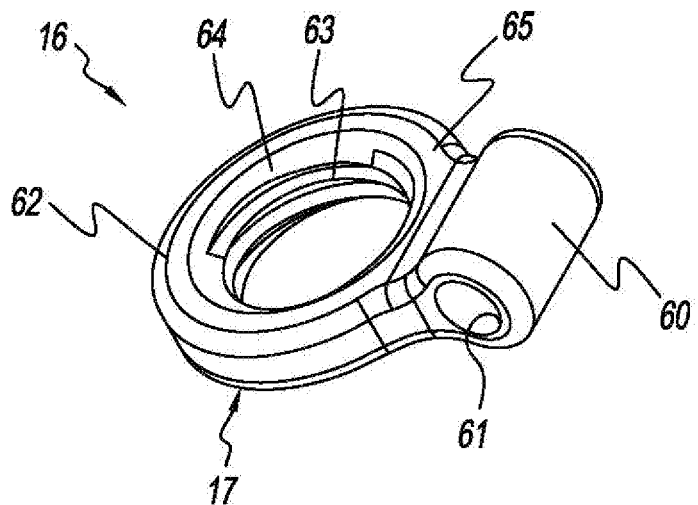
FIG. 13 is a view of a single bone screw plate or end of the dual pivot spine implant of FIG. 1.
Figure 14:
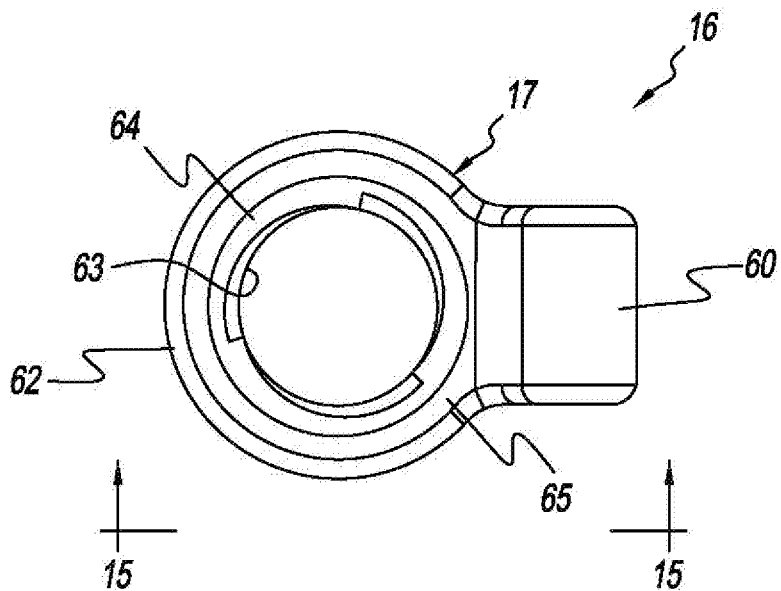
FIG. 14 is a top view of the single bone screw plate of FIG. 13.
Figure 15:
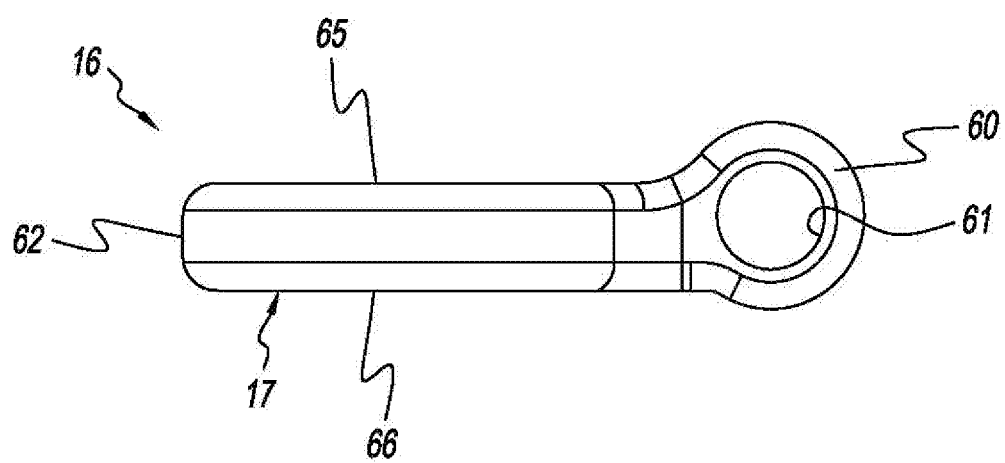
FIG. 15 is a side view of the single bone screw plate of FIG. 13 taken along line 15-15 of FIG. 14.
Figure 16:
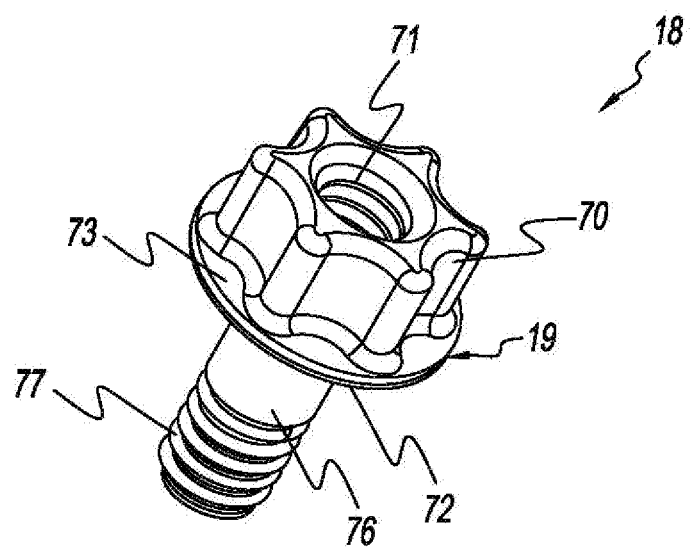
FIG. 16 is a view of a lag screw for forms of the present spine implant of FIG. 1 without a spacer.
Figure 17:
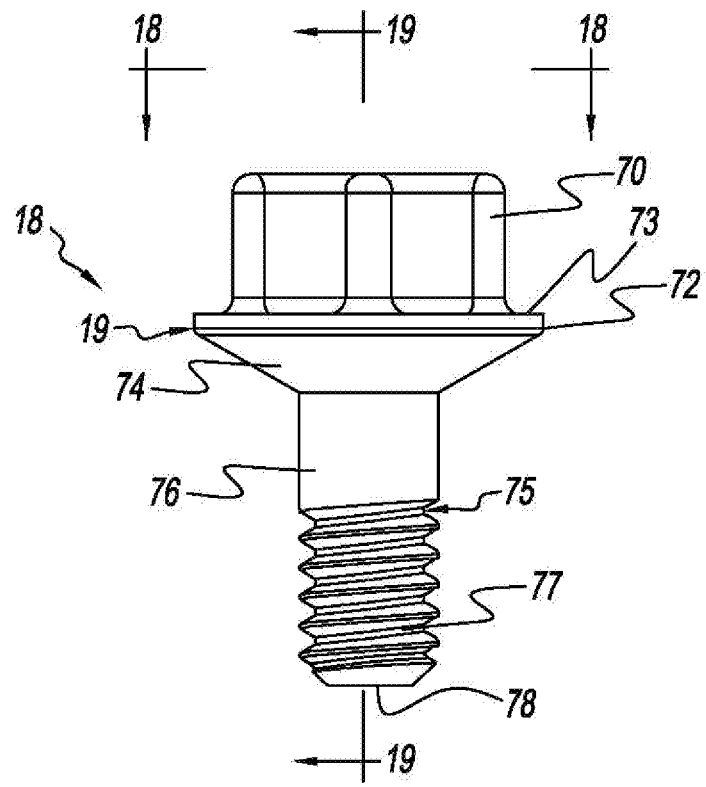
FIG. 17 is a side view of the lag screw of FIG. 16.
Figure 18:
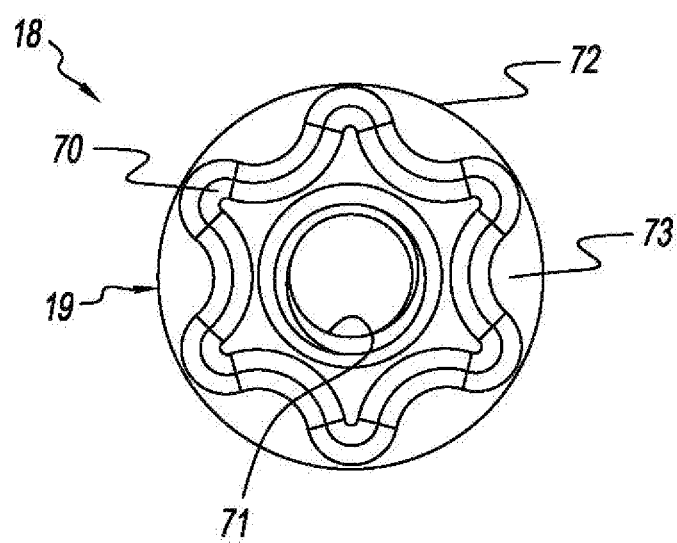
FIG. 18 is a top view of the lag screw of FIG. 16 taken along line 18-18 of FIG. 17.
Figure 19:
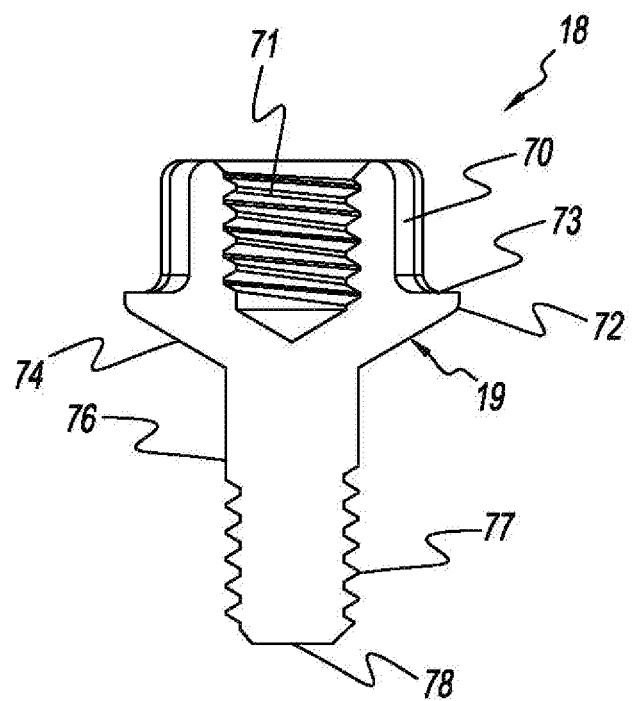
FIG. 19 is a sectional view of the lag screw of FIG. 16 taken along line 19-19 of FIG. 17.
Figure 20:
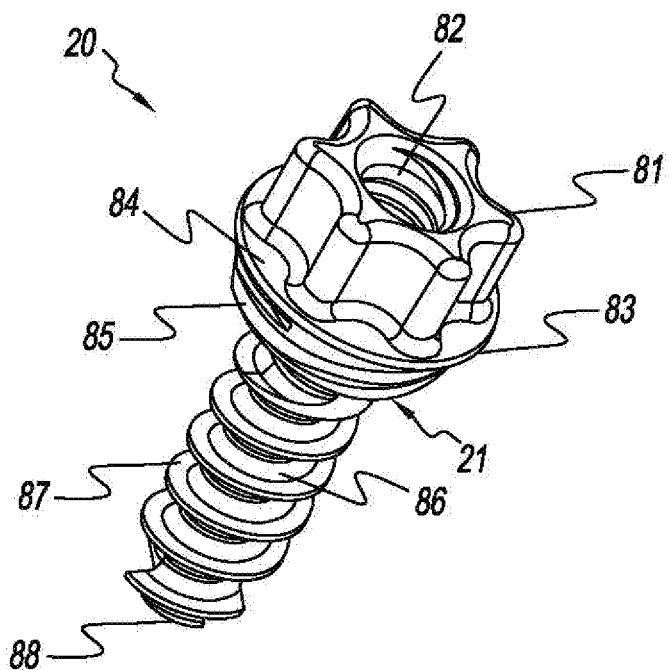
FIG. 20 is a view of a bone screw for all forms of the present spine implant.
Figure 21:
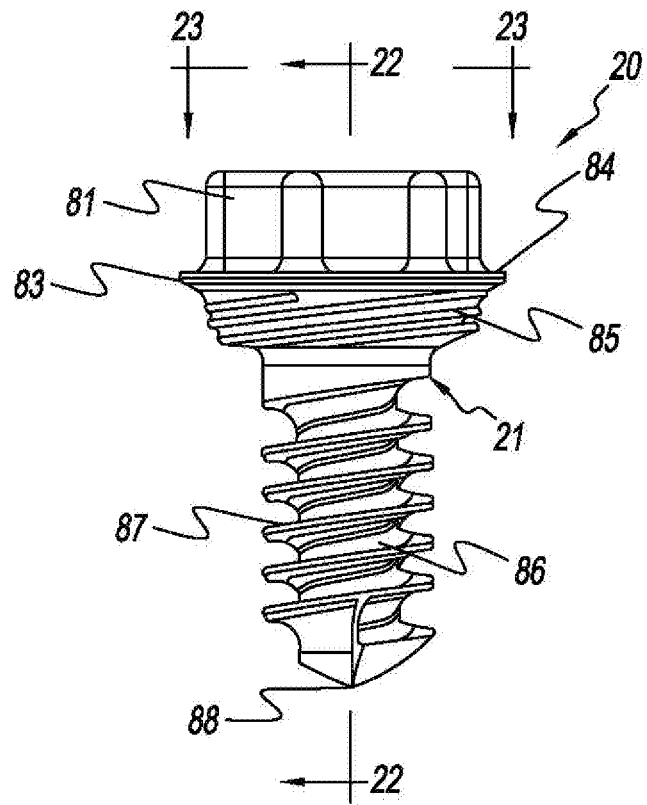
FIG. 21 is a side view of the bone screw of FIG. 20.
Figure 22:
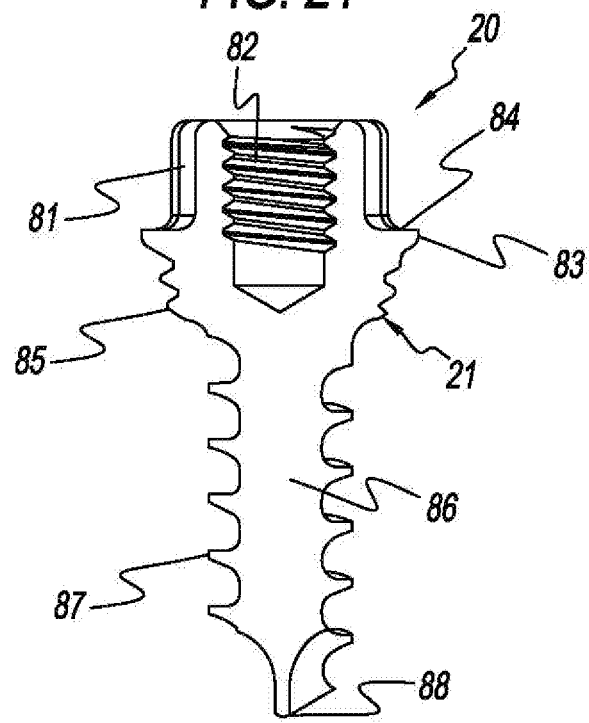
FIG. 22 is a sectional view of the bone screw of FIG. 20 taken along line 22-22 of FIG. 21.
Figure 23:
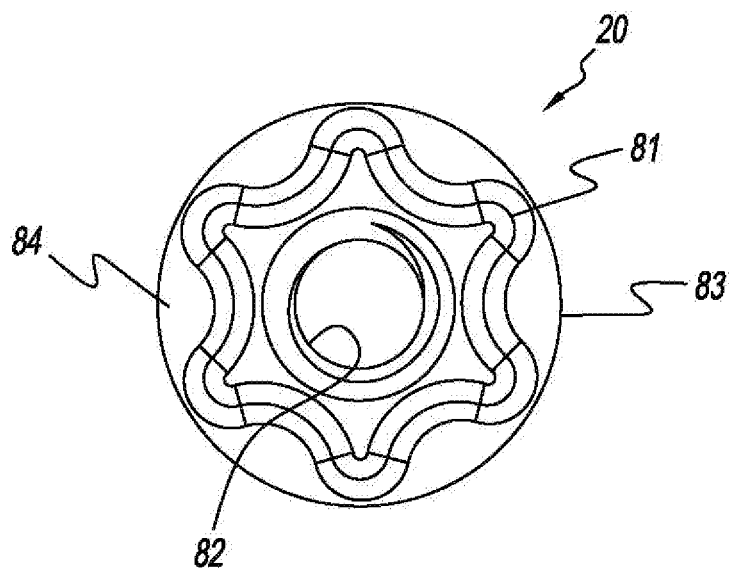
FIG. 23 is top view of the bone screw of FIG. 20 taken along line 23-23 of FIG. 21.

FIGS. 13-15 show the single bone screw plate 16. The single bone screw plate 16 has a body 17 with an upper side 65 and a lower side 66. The lower side 66 is substantially planar and is configured for placement against vertebral bone. The upper side 65 is also substantially planar. The body 17 has a boss, projection, extension or the like 60 having a bore 61 extending through the boss 60. The bore 61 is configured to receive the pivot pin 24. The boss 60 is sized for reception in the second notch 35 of the base plate 12. The boss 60 connects to the base plate 12 via a pivot pin 24.

A third, internally threaded bone screw bore 63 is provided at an end 62 of the body 17. The third, internally threaded bone screw bore 63 extends from the upper side 65 to the lower side 66. A countersink 64 is provided about the third, internally threaded bone screw bore 63 on the upper side 65 of the body 17. The third, internally threaded bone screw bore 63 is configured to receive and hold a bone screw 20. Particularly, the shaft 75 of the bone screw 20 is able to extend through the third, internally threaded bone screw bore 63 while the externally threaded underside 85 of the head 81 of the bone screw 20 threadedly mates with the third, internally threaded bone screw bore 63.

FIGS. 16-19 show the lag screw 18. The lag screw 18 is a form of a fastener for attaching or connecting the spacer 22 to the base plate 12. The lag screw 18 has a body 19 generally defining a head 70 and a shaft 86. The head 70 is in the form of a hexalobe but other configurations may be used. The hexalobe head 70 allows a hexalobe driver or installation tool/instrument (not shown) to install the lag screw 18. The hexalobe head 70 also has a threaded socket 71 that allows the hexalobe driver/installation tool/instrument to temporarily connect to the head 70 for a more positive installation/rotation of the lag screw 18. As readily seen in the figures, the hexalobe head 70 is situated on a round platform 72 that projects radially outward about the hexalobe head 70 such that the hexalobe head 70 seems to rest on the platform 72. As such, the platform 72 has an upper surface 73 that radially surrounds the hexalobe head 70.

The platform 72 has a lower portion 74 that slants or angles radially inward in a conical section. The angled lower portion 74 is received by and fits into the countersink 45 of the bore 44 of the base plate 12. A shaft 75 extends axially downwardly from the angled lower portion 74. The shaft 75 has a neck or first shaft portion 76 having a smooth outer surface. The smooth outer surface of the first shaft portion 76 is what is received in the bore 44 of the base plate 12. The shaft 75 has an externally threaded second shaft portion 77 situated axially downward from the first shaft portion 76. The second shaft portion 77 is configured for reception in the threaded bore 93 of the spacer 22. The axial end 78 of the shaft 75 is generally planar—coinciding with the general shape of the threaded bore 93 of the spacer 22.

FIGS. 20-23 show the bone screw 20. The bone screw 20 is a form of a bone fastener for attaching or connecting the bone screw plates of the present implant to vertebral bone. The bone screw 20 has a body 21 generally defining a head 81 and a shaft 86. The head 81 is in the form of a hexalobe but other configurations may be used. The hexalobe head 81 allows a hexalobe driver or installation tool/instrument (not shown) to install the bone screw 20. The hexalobe head 81 also has a threaded socket 82 that allows the hexalobe driver/installation tool/instrument to temporarily connect to the head 81 for a more positive installation/rotation of the bone screw 20. As readily seen in the figures, the hexalobe head 81 is situated on a round platform 83 that projects radially outward about the hexalobe head 81 such that the hexalobe head 81 seems to rest on the platform 83. As such, the platform 83 has an upper surface 84 that radially surrounds the hexalobe head 81.

The platform 83 has a lower portion 85 that slightly slants or angles radially inward. The lower portion 85 has external threading that is received by and fits into the internally threaded bone screw bores of the bone screw plates. This provides a positive connection between the bone screw plate and the bone screw. It also aids in preventing or ameliorating bone screw backout. A shaft 86 extends axially downwardly from the externally threaded lower portion 85 and terminates in a tip 88. The shaft 86 has external threading 87 configured for reception in vertebral bone.

Figure 24:
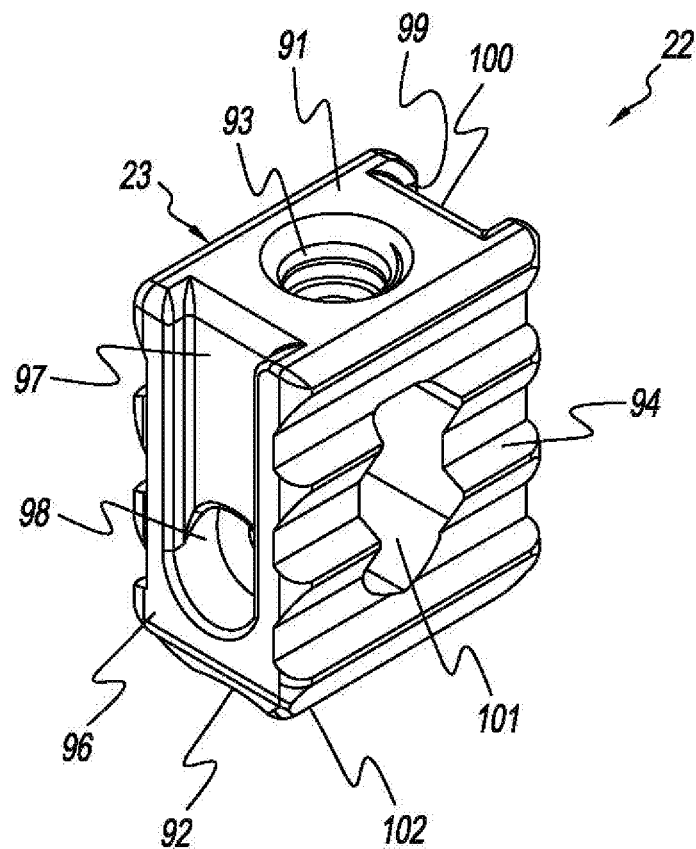
FIG. 24 is a view of a spacer for the spine implant of FIG. 1 and other forms thereof.
Figure 25:
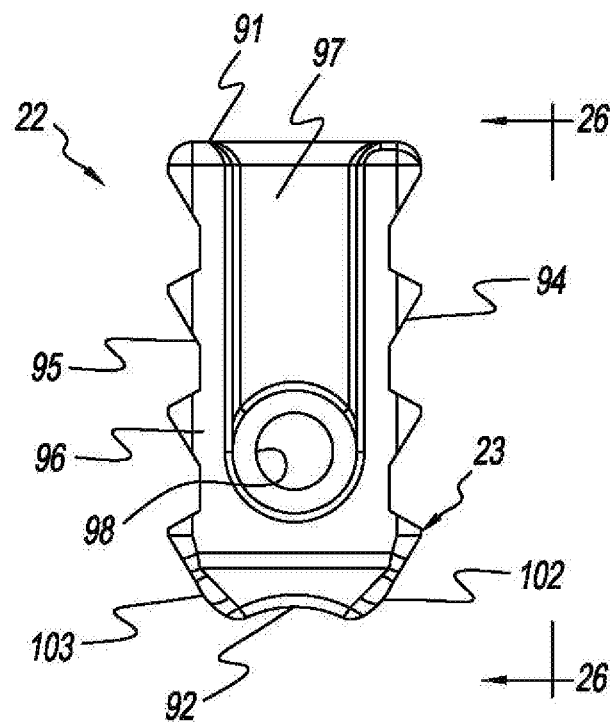
FIG. 25 is a lateral side view of the spacer of FIG. 24.
Figure 26:
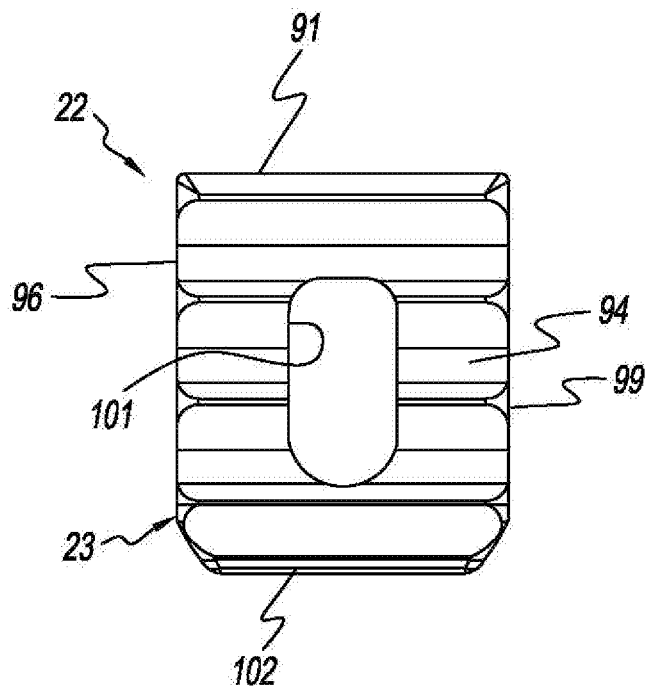
FIG. 26 is side view of the spacer of FIG. 24.

FIGS. 24-26 show the spacer, block, wedge or the like 22 (collectively, spacer 22) that is part of the components of the present spinal implant when used as a spinal facet joint fixation. The spacer 22 has a body 23 in the general or substantial shape of a rectangular block that is configured for placement and retention between vertebral bone such as, but not limited to, adjacent spinal facet joints (zygapophysial joints, zygapophyseal, apophyseal, or Z-joints) between the articular processes of two adjacent vertebrae (see, e.g., FIGS. 29 and 30). The spacer 22 has a substantially planar top 91 and a curved bottom 92 opposite the planar top 91. The planar top 91 is configured to abut the lower surface 47 of the base plate 12. A threaded bore 93 is disposed in the planar top 91 that is configured to receive the threaded lower shaft portion 77 of the lag screw 18 in order to connect the spacer 22 to the base plate 12.

The body 23 of the spacer 22 defines a first serrated side or face 94 and a second serrated side or face 95 opposite the first serrated side 94. The serrations provide gripping of the sides against vertebral bone. The first and second sides 94, 95 may have structuring other than serrations to provide the desired or requisite gripping or holding of the spacer 22. The upper surface of the first serrated side 94 is generally planar with the top 91 while the lower surface of the first serrated side 94 is angled 102 as it meets the curved bottom 92. The upper surface of the second serrated side 95 is generally planar with the top 91 while the lower surface of the second serrated side 95 is angled 103 as it meets the curved bottom 92.

The body 23 of the spacer 22 further defines a first lateral end 96 situated between one side of the first serrated face 94 and the second serrated face 95, and a second lateral end 99 opposite the first lateral end and situated between another side of the first serrated face 94 and the second serrated face 95. The first lateral end 96 has an elongated channel, groove or the like 97 extending from the top 91 to proximate the curved bottom 92. A bore 98 is provided in the channel 97 proximate the curved bottom 92. The channel 97 and associated bore 98 provides a manner of implanting or installing the spacer 22 via an installation/implantation tool/instrument (not shown). The second lateral end 99 has an elongated channel, groove or the like 100 extending from the top 91 to proximate the curved bottom 92. A bore 101 is provided in the channel 100 proximate the curved bottom 92. The channel 100 and associated bore 101 provides a manner of implanting or installing the spacer 22 via the installation/implantation tool/instrument (not shown).

Figure 27:
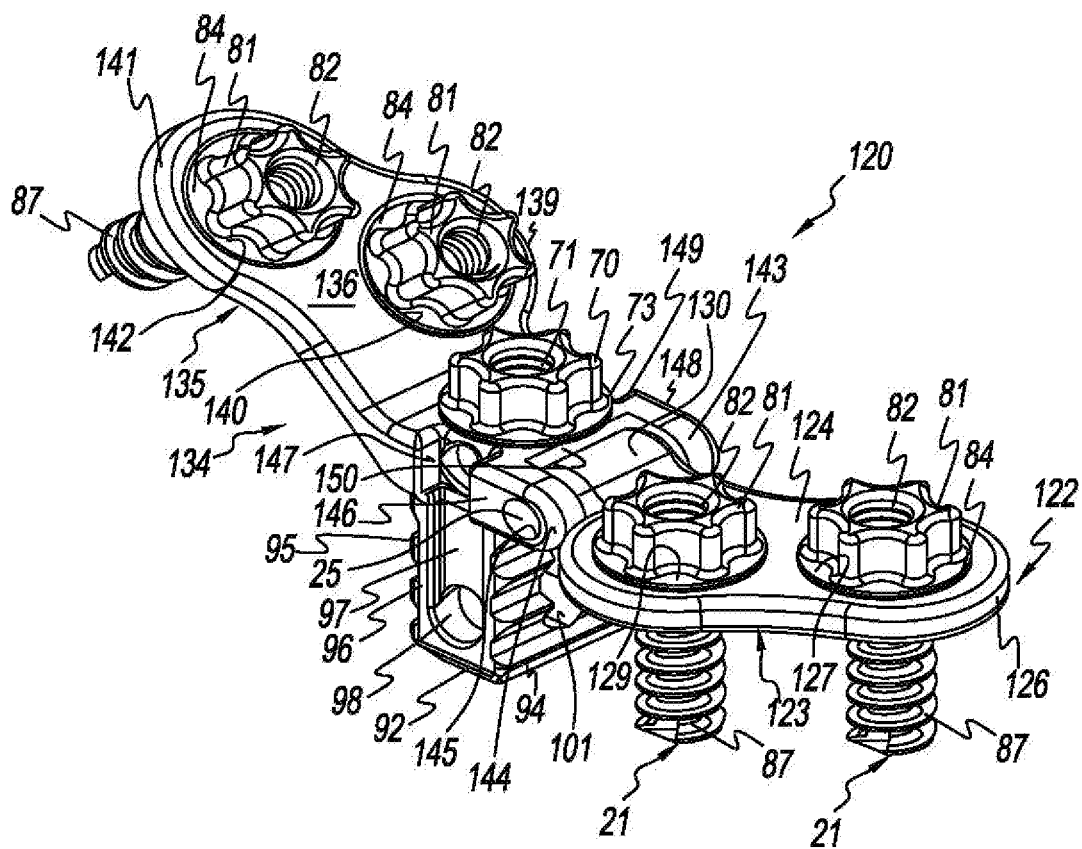
FIG. 27 is a view of a single pivot form of the present spine implant.
Figure 28:
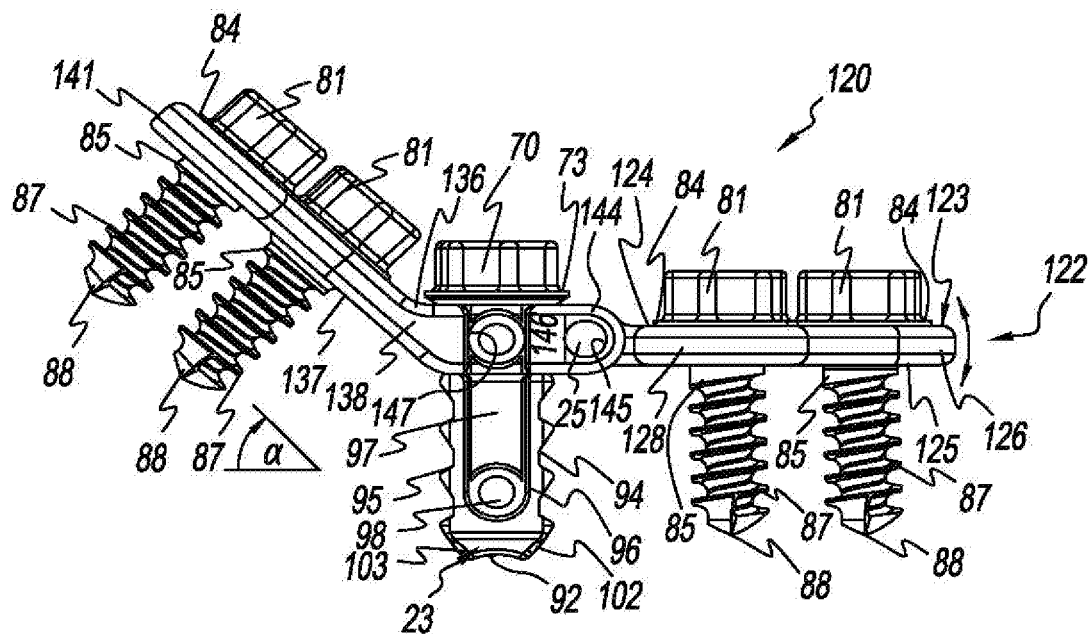
FIG. 28 is a side view of the single pivot spine implant FIG. 27.

FIGS. 27 and 28 show another form of the present spine implant, generally designated 120. The spine implant 120 is a fixed version spine implant facet joint fixation version with two, dual bone screw plates. The spine implant 120 is similar to the spine implant 10 but rather than two angularly adjustable (pivoting) bone screw plates, the spine implant 120 has one angularly adjustable (pivoting) bone screw plate 122 and a base plate 134 having a fixed angle ($\alpha$) dual bone screw plate 135. The angle ($\alpha$) may be any degree as desired. The base plate 134 connects with the spacer 22 of the implant 10 by the lag screw 18 of the implant 10 in the same manner as the implant 10.

The dual bone screw plate 122 has a body 123 with a substantially planar upper surface 124 and a substantially planar lower surface 125. The lower surface 125 is configured to contact vertebral bone. A pivot boss 127 extends from one end of the body 123 and is configured for reception in a notch 150 of the base plate 134. The notch 150 is formed by a first flange 143 extending from a first lateral side 148 and a second flange 144 extending from a second lateral side 146. The first flange 143 has a bore (not seen) therein that is sized to receive a pivot pin 24. The second flange 144 has a bore 145 therein that is sized to receive the pivot pin 24. The pivot boss 127 is thus pivotally coupled to the base plate 134 such that the dual bone screw plate 122 is angularly adjustable relative to the base plate 134.

The dual bone screw plate 122 has a first end 126 having a first bone screw bore 127 having inner threading (not seen) in the same configuration and for the same purpose as the inner threading of the bone screw bores of the dual bone screw plate 14 and the single bone screw plate 16. A second end 128 of the dual bone screw plate 122 has a second bone screw bore 129 having inner threading (not seen) in the same configuration and for the same purpose as the inner threading of the bone screw bores of the dual bone screw plate 14 and the single bone screw plate 16. Each bone screw bore 127, 129 is configured to receive and retain a bone screw 20.

The base plate 134 includes a first lateral notch 149 in the first lateral side 148 that aligns with the channel 100 of the spacer 22 in like manner and function as the notch 42 of the base plate 12 and the channel 100 of the spacer 22 of the implant 10. The base plate 134 includes a second lateral notch 147 in the second lateral side 146 that aligns with the channel 97 of the spacer 22 in like manner and function as the notch 40 and the channel 97 of the spacer of the implant 10.

The fixed angle dual bone screw plate 135 extends at a fixed angle α via a neck 138 from the base plate 134. The angle α may be chosen as desired. The fixed angle dual bone screw plate 135 has a substantially planar upper surface 136 and a substantially planar lower surface 137. The lower surface 137 is configured to contact vertebral bone. The fixed angle dual bone screw plate 135 has a first end 141 having a first bone screw bore 142 having inner threading (not seen) in the same configuration and for the same purpose as the inner threading of the bone screw bores of the dual bone screw plate 14 and the single bone screw plate 16. A second end 139 of the dual bone screw plate 135 has a second bone screw bore 145 having inner threading (not seen) in the same configuration and for the same purpose as the inner threading of the bone screw bores of the dual bone screw plate 14 and the single bone screw plate 16. Each bone screw bore 142, 145 is configured to receive and retain a bone screw 20.

It should be appreciated that while the fixed angle spine implant 120 is shown with a spacer 22 and thus is configured for use as a spinal facet joint fixation implant, the fixed angle spine implant 120 may be used without a spacer and thus would be configured for use in a laminoplasty.

FIGS. 29 and 30 show spinal facet joint fixation use of the spine implant 10. FIGS. 29 and 30 specifically show two adjacent vertebra V1, V2 whose facet joint between two articular processes AP1, AP2 of the adjacent vertebra V1, V2 have been fixed by the implant 10. The spacer 22 is situated in the facet joint while the dual bone screw plate 14 is affixed to the lower articular process AP2 of the lower vertebra V2 and the single bone screw plate 16 is affixed to the upper articular process AP1 of the upper vertebra V1.

FIG. 31 shows laminoplasty use of the spine implant 10a without the spacer 22. A single vertebra V3 is shown whose lamina has been cut and distracted into a first lamina portion LP1 and a second lamina portion LP2. The spine implant 10a bridges or connects the first and second lamina portions LP1 and LP2. The single bone screw plate 16 is shown affixed to the first lamina portion LP1, while the dual bone screw plate 14 is shown affixed to the second lamina portion LP2.

It should be appreciated that dimensions of the components, structures, and/or features of the present spine implant may be altered as desired within the scope of the present disclosure.

What is claimed is:

1. A spine implant for spinal facet joint fixation or connecting distracted spinal lamina portions in a laminoplasty, the spine implant comprising:

a base plate having a planar upper surface, a planar lower surface opposite the upper surface, a first lateral side between the planar upper surface and the planar lower surface, a second lateral side opposite the first lateral side and between the planar upper surface and the planar lower surface, a first end between the first lateral side and the second lateral side, a second end opposite the first end and between the first lateral side and the second lateral side, a first notch at the first end, the first notch formed by a first projection extending from the first lateral side, the first projection having a first through-hole, and a second projection extending from the second lateral side, the second projection having a second through-hole, and a second notch at the second end, the second notch formed by a third projection extending from the first lateral side, the third projection having a third through-hole, and a fourth projection extending from the second lateral side, the fourth projection having a fourth through-hole;

a first bone screw plate configured to attach to first vertebral bone of a vertebra, the first bone screw plate having a planar top surface, a planar bottom surface opposite the planar top surface, a first bone screw plate boss configured for pivotal reception in the first notch at the first end of the base plate such that the first bone screw plate is angularly adjustable relative to the base plate, the first bone screw plate boss including a fifth through-hole, a first bone screw plate bore extending from the planar top surface to the planar bottom surface and defining a first bone screw plate bore interior wall, and first threading on the first bone screw plate bore interior wall, the first bone screw plate bore and the first threading of the first bone screw plate bore interior wall configured to receive and hold a first bone screw;

a second bone screw plate configured to attach to second vertebral bone of a vertebra, the second bone screw plate having a planar superior surface, a planar inferior surface opposite the planar superior surface, a second bone screw plate boss configured for pivotal reception in the second notch at the second end of the base plate such that the second bone screw plate is angularly adjustable relative to the base plate, the second bone screw plate boss including a sixth through-hole, a second bone screw plate first bore extending from the planar superior surface to the planar inferior surface and defining a second bone screw plate first bore interior wall, second threading on the second bone screw plate first bore interior wall, the second bone screw plate first bore and the second threading of the second bone screw plate first bore interior wall configured to receive and hold a second bone screw, a second bone screw plate second bore extending from the planar superior surface to the planar inferior surface and defining a second bone screw plate second bore interior wall, and third threading on the second bone screw plate second bore interior wall, the second bone screw plate second bore and the third threading of the second bone screw plate second bore interior wall configured to receive and hold a third bone screw a first pin received in the first through-hole of the first projection, the fifth through-hole of the first bone screw plate boss, and the second through-hole of the second projection to pivotally couple the first bone screw plate to the base plate;

a second pin received in the third through-hole of the third projection, the sixth through-hole of the second bone screw plate boss, and the fourth through-hole of the fourth projection to pivotally couple the second bone screw plate to the base plate;

a base plate bore in the base plate extending from the planar upper surface to the planar lower surface;

a rectangular block configured to wedge between the first vertebral bone of a vertebra and the second vertebral bone of a vertebra, the rectangular block having a flat top, a concave bottom, a first serrated face extending between the flat top and the concave bottom, a second serrated face opposite the first serrated face and extending between the flat top and the concave bottom, a first side between the first serrated face and the second serrated face, a second side opposite the first side and between the first serrated face and the second serrated face, the first side having a first slot extending from the flat top to proximate the concave bottom and configured to receive a first portion of an installation instrument, the second side having a second slot extending from the flat top to proximate the concave bottom and configured to receive a second portion of the installation instrument, a threaded hole in the flat top, an opening extending through and between the first serrated face of the rectangular block and the second serrated face of the rectangular block, a first lateral hole in a first lower portion of the first slot of the first side of the rectangular block, and a second lateral hole in a second lower portion of the second slot of the second side of the rectangular block; and a connector having an externally threaded shaft configured to extend through the base plate bore and into the threaded hole of the rectangular block for coupling the rectangular block to the planar lower surface of the base plate.

2. A spine implant for spinal facet joint fixation or connecting distracted spinal lamina portions in a laminoplasty, the spine implant comprising:

a first plate having a planar upper surface, a planar lower surface opposite the upper surface, a first lateral side between the planar upper surface and the planar lower surface, a second lateral side opposite the first lateral side and between the planar upper surface and the planar lower surface, a first end between the first lateral side and the second lateral side, a second end opposite the first end and between the first lateral side and the second lateral side, a first notch at the first end, the first notch formed by a first projection extending from the first lateral side, the first projection having a first through-hole, and a second projection extending from the second lateral side, the second projection having a second through-hole, and a second notch at the second end, the second notch formed by a third projection extending from the first lateral side, the third projection having a third through-hole, and a fourth projection extending from the second lateral side, the fourth projection having a fourth through-hole;

a second plate configured to attach to first vertebral bone of a vertebra, the second plate having a planar top surface, a planar bottom surface opposite the planar top surface, a second plate flange configured for pivotal reception in the first notch at the first end of the first plate such that the second plate is angularly adjustable relative to the first plate, the second plate flange including a fifth through-hole, a second plate bore extending from the planar top surface to the planar bottom surface and defining a second plate bore interior wall and a second plate bore center, and first threading on the second plate bore interior wall, the second plate bore and the first threading of the second plate bore interior wall configured to receive and hold a first bone screw;

a third plate configured to attach to second vertebral bone of a vertebra, the third plate having a planar superior surface, a planar inferior surface opposite the planar superior surface, a third plate flange configured for pivotal reception in the second notch at the second end of the first plate such that the third plate is angularly adjustable relative to the first plate, the third plate flange including a sixth through-hole, a third plate first bore extending from the planar superior surface to the planar inferior surface and defining a third plate first bore interior wall and a third plate first bore center, second threading on the third plate first bore interior wall, the third plate first bore and the second threading of the third plate first bore interior wall configured to receive and hold a second bone screw, a third plate second bore extending from the planar superior surface to the planar inferior surface and defining a third plate second bore interior wall and a third plate second bore center, and third threading on the third plate second bore interior wall, the third plate second bore and the third threading of the third plate second bore interior wall configured to receive and hold a third bone screw;

a first pin received in the first through-hole of the first projection, the fifth through-hole of the second plate flange, and the second through-hole of the second projection to pivotally couple the second plate to the first plate, the first pin defining a first pivot axis, wherein the second plate bore center is situated perpendicular to the first pivot axis;

a second pin received in the third through-hole of the third projection, the sixth through-hole of the third plate flange, and the fourth through-hole of the fourth projection to pivotally couple the third plate to the first plate, the second pin defining a second pivot axis, wherein the third plate first bore center is situated skew from a perpendicular to the second pivot axis, and the third plate second bore center is situated skew from the perpendicular to the second pivot axis and offset from the third plate first bore center; and a rectangular spacer configured for placement between the first vertebral bone of a vertebra and the second vertebral bone of a vertebra, the rectangular spacer having a flat top, a concave bottom, a first serrated face extending between the flat top and the concave bottom, a second serrated face opposite the first serrated face and extending between the flat top and the concave bottom, a first side between the first serrated face and the second serrated face, a second side opposite the first side and between the first serrated face and the second serrated face, the first side having a first slot extending from the flat top to proximate the concave bottom and configured to receive a first portion of an installation instrument, the second side having a second slot extending from the flat top to proximate the concave bottom and configured to receive a second portion of the installation instrument, and a threaded hole in the flat top.

3. The spine implant of claim 2, further comprising:
a first plate bore in the first plate extending from the planar upper surface to the planar lower surface; and
a connector having an externally threaded shaft configured to extend through the first plate bore and into the threaded hole of the rectangular spacer for coupling the rectangular spacer to the planar lower surface of the first plate.

4. The spine implant of claim 3, wherein the rectangular spacer further comprises:
an opening extending through and between the first serrated face of the rectangular spacer and the second serrated face of the rectangular spacer;
a first lateral hole in a first lower portion of the first slot of the first side of the rectangular spacer; and
a second lateral hole in a second lower portion of the second slot of the second side of the rectangular spacer.

5. The spine implant of claim 3, wherein:
the first plate has a countersink in the planar upper surface surrounding the first plate bore.

\* \* \* \* \*